(12) United States Patent
Karlsen

(10) Patent No.: US 7,910,294 B2
(45) Date of Patent: Mar. 22, 2011

(54) LIGAND DETECTION METHOD

(75) Inventor: Frank Karlsen, Klokkarstua (NO)

(73) Assignee: Norchip A/S, Klokkarstua (NO)

( * ) Notice: Subject to any disclaimer, the term of this patent is extended or adjusted under 35 U.S.C. 154(b) by 462 days.

(21) Appl. No.: 10/433,548

(22) PCT Filed: Dec. 5, 2001

(86) PCT No.: PCT/GB01/05388
§ 371 (c)(1),
(2), (4) Date: Dec. 5, 2003

(87) PCT Pub. No.: WO02/46464
PCT Pub. Date: Jun. 13, 2002

(65) Prior Publication Data
US 2004/0076983 A1    Apr. 22, 2004

(30) Foreign Application Priority Data

Dec. 5, 2000 (GB) .................................. 0029617.8

(51) Int. Cl.
C12Q 1/68 (2006.01)
G01N 33/53 (2006.01)
C12P 19/34 (2006.01)

(52) U.S. Cl. ............................................ 435/6; 435/7.1

(58) Field of Classification Search .................. None
See application file for complete search history.

(56) References Cited

U.S. PATENT DOCUMENTS

| 5,656,731 A * | 8/1997 | Urdea ........................ 530/391.1 |
| 5,665,539 A * | 9/1997 | Sano et al. ........................ 435/6 |
| 5,700,667 A * | 12/1997 | Marble et al. ................. 435/91.3 |
| 5,854,033 A * | 12/1998 | Lizardi .............................. 435/6 |
| 6,255,060 B1 * | 7/2001 | Eberwine et al. ............. 435/7.92 |

FOREIGN PATENT DOCUMENTS

| WO | WO93/01498 | * | 1/1993 |
| WO | WO 94/26932 A1 | | 11/1994 |
| WO | WO 96/32640 A1 | | 10/1996 |
| WO | WO 97/32044 A1 | | 9/1997 |
| WO | WO98/22624 | * | 5/1998 |
| WO | WO 98/22624 A1 | | 5/1998 |
| WO | WO 99/63109 A1 | | 12/1999 |
| WO | WO 01/31056 A2 | | 5/2001 |

OTHER PUBLICATIONS

Sanna PP et al. "Rapid induction of tumor necrosis factor alpha in the cerebrospinal fluid after intracerebroventricular injuection of lipopolysaccharide revealed by sensitive capture immuno-PCR assay", PNAS, 1995, vol. 92, p. 272-275.*
Sims PW, et a. "Immunopolymerase chain reaction using Real-Time polymerase chain reaction for detection", Analytical Biochemistry, 1000, vol. 281, p. 230-232.*
Chang TC, et al. "A modified immuno-polymerase chain reaction for the detection of beta-glucuronidase from *Escherichia coli*" J. of Immunological Methods, 1997, vol. 208, p. 35-42.*
Lie YS, and Petropolous CJ, "Advances in quantitative PCR technology, 5' nuclease assays", Current Opin. Biotech., 1998, vol. 9, p. 43-48.*
Leone G, et al. "Molecular beacon probes combined with amplification by NASBA enable homogeneous, real-time detection of RNA", Nucleic Acids Research, 1998, vol. 26, No. 9, p. 2150-2155.*
Cao Y, et al. "In-situ immuno-PCR to detect antigens", The Lancet, 2000, vol. 356, p. 1002-1003.*
Sano T, et al. "Immuno-PCR: very sensitive antigen detection by means of specific antibody-DNA conjugates", Science, 1992, vol. 258, p. 120-122.*
Ruzicka V, et al. "Immuno-PCR with a commercially available avidin system", Science, 1993, vol. 260, p. 698-699.*
Vandamme et al. (Journal of Virological Methods, 1995, vol. 52, p. 121-132).*
Gulliksen et al. (2004, Anal. Chem., 76, p. 9-14).*
Sims, et al., "Immunopolymerase Chain Reaction Using Real-Time Polymerase Chain Reaction for Detection," Analytical Biochemistry, May 2000, vol. 281, pp. 230-232.
Leone, et al., "Molecular Beacon Probes Combined with Amplification by NASBA enable Homogeneous, Real-time Detection of RNA," Nucleic Acids Research, 1998, vol. 26, No. 9, pp. 2150-2155.
Strunk, et al., "Machines for Automated Evolution Experiments In Vitro Based on the Serial-transfer Concept," Biophysical Chemistry, 1997, vol. 66, pp. 193-202.

* cited by examiner

*Primary Examiner* — Stephanie K Mummert
(74) *Attorney, Agent, or Firm* — Wolf, Greenfield & Sacks, P.C.

(57) ABSTRACT

There is disclosed a sensitive method for specific detection of ligands comprising the steps of (a) contacting the sample with reagents capable of forming a reagent complex, which reagent complex comprises a receptor capable of specifically binding to said ligand and a nucleic acid molecule; and (b) detecting any complexes formed by binding of the receptor part of said reagent complex to ligand present in the sample by specifically detecting the presence of the nucleic acid molecule by amplifying a region of the nucleic acid and simultaneously detecting products of the amplification reaction in real-time.

15 Claims, 4 Drawing Sheets

FIGURE 2
EXAMPLES OF LINKERS
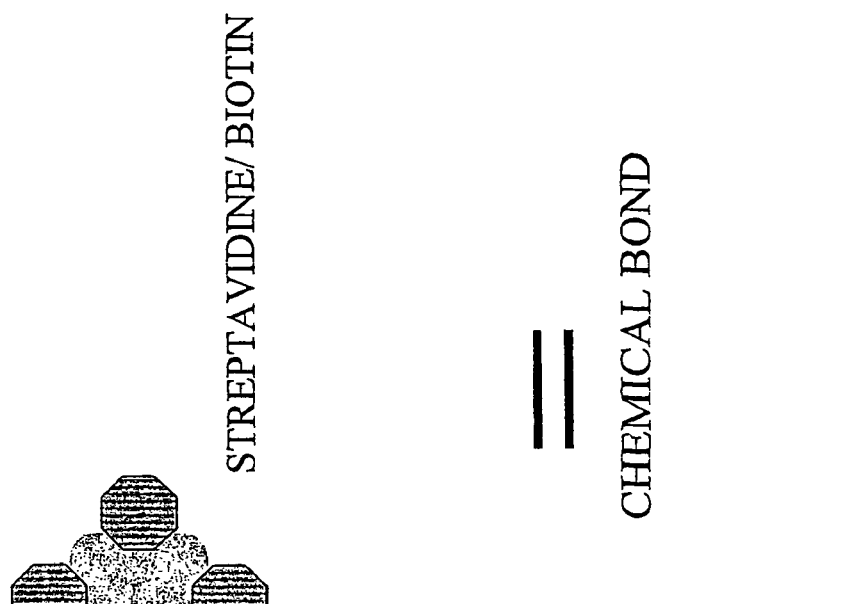
STREPTAVIDINE/ BIOTIN
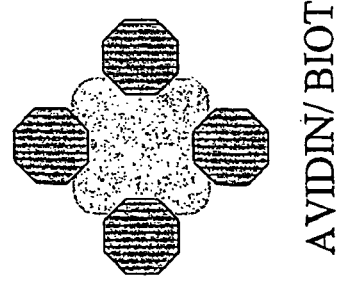
AVIDIN/ BIOTIN
CHEMICAL BOND
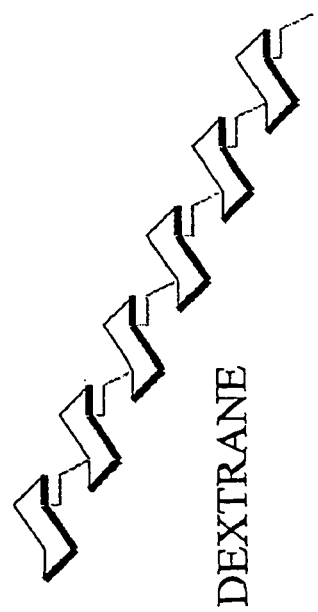
DEXTRANE

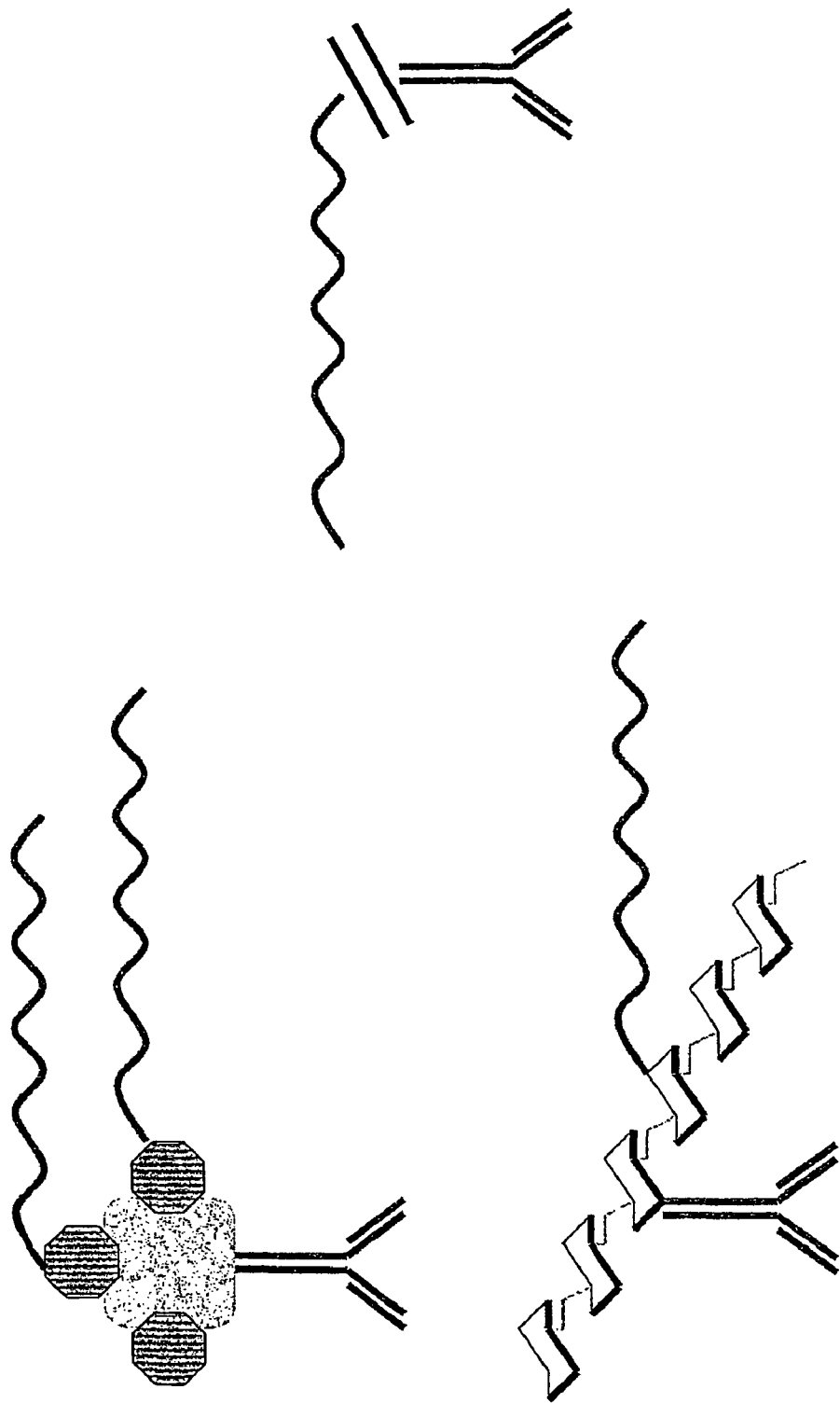
FIGURE 3 EXAMPLES OF CONJUGATES USING DIFFERENT LINKERS

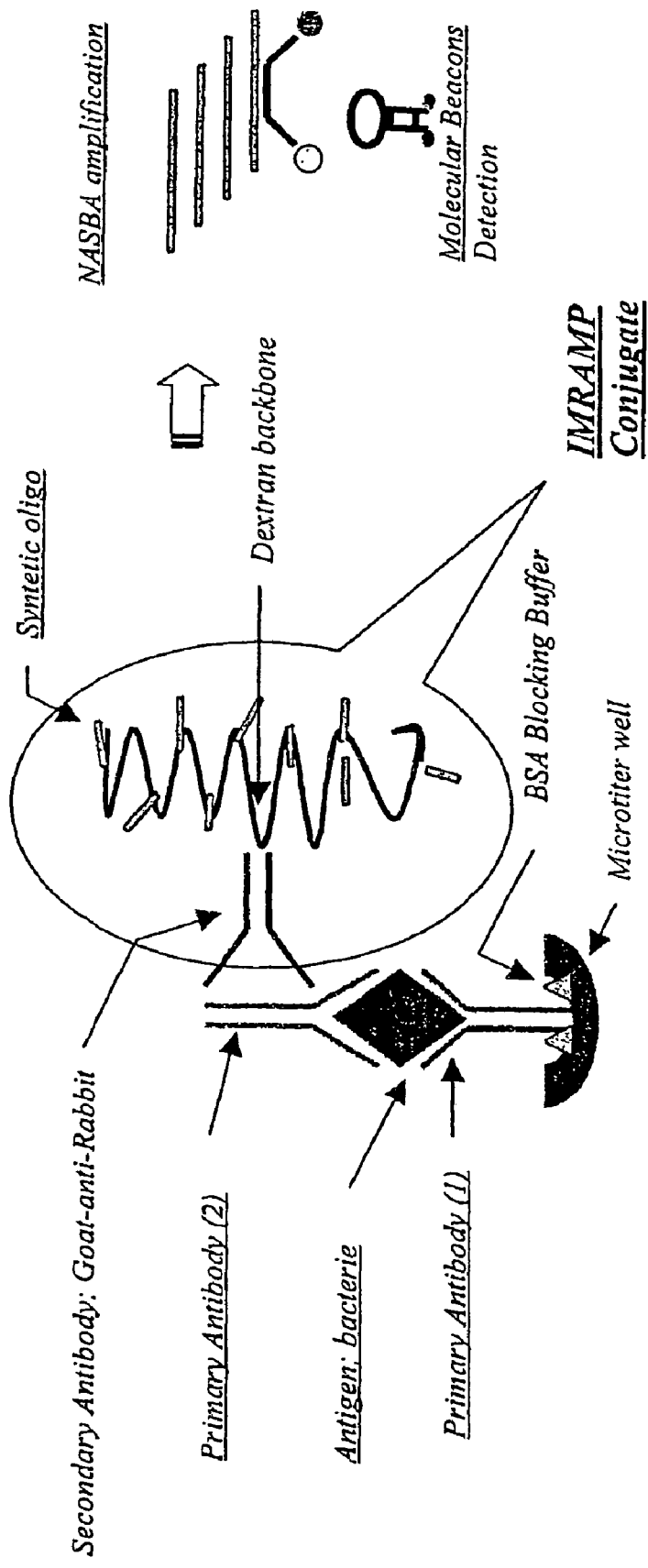

LIGAND DETECTION METHOD

RELATED APPLICATIONS

This application is a national stage filing under 35 U.S.C. §371 of PCT International application PCT/GB01/05388, filed Dec. 5, 2001, which was published under PCT Article 21(2) in English.

FIELD OF THE INVENTION

The invention relates to a sensitive method for specific detection of ligands.

BACKGROUND TO THE INVENTION

Immunological detection is currently the method of choice for ligand detection in the field of diagnostics. However, traditional immunological detection methods, such as the enzyme-linked immunosorbent assay (ELISA), suffer from a lack of sensitivity and/or specificity when it comes to the detection of ligands present at a very low concentration. Standard ELISA has a maximum sensitivity of approximately 10 000 cells or copies of target per unit. Normally the sensitivity is not above 100 000 cells or targets. Concentration of proteins by immunomagnetic methods may result in an increase in sensitivity to detect down to one human cell in research studies, but this is largely due to the large size of human cells. Maximum sensitivity for the detection of bacterial cells remains of the order of 1000 cells, even with the use of immunomagnetic antibody methods. Thus there remains a need for more sensitive methods of immunological detection.

U.S. Pat. No. 5,665,539 describes an "immuno-polymerase chain reaction" method for immunological detection. This method is based on the use of a specific antibody conjugated to a double-stranded DNA molecule. Complexes formed by binding of the antibody conjugate to an antigen are detected by first amplifying a region of the double-stranded DNA using PCR and then detecting the amplification products.

The present inventors have developed an alternative method for sensitive antigen (ligand) detection which is based on real-time amplification of a nucleic acid marker. This method combines the specificity of immunological reactions with the sensitivity of nucleic acid amplification and can be used for real-time quantitative measurement.

DESCRIPTION OF THE INVENTION

In a first aspect the invention provides a method for detecting a ligand in a sample, which method comprises steps of:
(a) contacting the sample with reagents capable of forming a reagent complex, which reagent complex comprises a receptor capable of specifically binding to said ligand and a nucleic acid molecule; and
(b) detecting any complexes formed by binding of the receptor part of said reagent complex to ligand present in the sample by specifically detecting the presence of the nucleic acid molecule by amplifying a region of the nucleic acid and simultaneously detecting products of the amplification reaction in real-time.

The invention is based on the combination of a specific ligand/receptor binding reaction and a detection step involving detection of a nucleic acid marker by amplification and real-time detection of the amplification products. The first part of the method of the invention is therefore analogous to a standard ligand/receptor binding assay, such as for example an immunoassay.

The receptor can be essentially any molecule which exhibits binding specificity for the ligand in question. Antibodies are particularly preferred, also antibody fragments which retain antigen binding specificity, for example F(ab')$_2$ fragments. Other suitable receptors include enzymes, hormone receptors, lectins etc. This list is not intended to be exhaustive.

The nucleic acid molecule is used as a marker to allow detection of specific ligand/receptor binding. Most preferably the nucleic acid marker is partially or completely single-stranded. The use of a nucleic acid marker provides significant advantages over more conventional markers, such as enzyme or fluorescent markers, as the step of detecting the nucleic acid may involve an amplification reaction. The amplification step substantially increases the sensitivity of the detection method.

The nucleic acid marker is most preferably a single-stranded DNA but single-stranded RNA markers may also be used. The invention also contemplates the use of synthetic RNA and DNA analogues, such as, for example, nucleic acids incorporating non-natural or derivatized bases and non-natural backbone linkages.

It is essential that the nucleic acid molecule is linked to the receptor molecule so that the amount of nucleic acid present may be taken as an indication of the amount of receptors bound to ligand in the sample. The single-stranded nucleic acid may be directly linked to the receptor but more usually it will be indirectly linked to the receptor via one or more linking molecules. For example, the single-stranded nucleic acid molecule may be linked to the receptor via a secondary receptor which specifically binds to the ligand-binding receptor. Furthermore, the single-stranded nucleic acid may be linked to the ligand-binding receptor or to the secondary receptor via conjugation to components of a biological binding pair, such as biotin/avidin or biotin/streptavidin. The term "linkage" therefore encompasses linkage via binding interactions.

In one embodiment the receptor and the single-stranded nucleic acid molecule may be linked to give a reagent complex in a separate step, prior to commencing the detection procedure. In a preferred embodiment, the nucleic acid may be linked to the ligand-binding receptor via formation of a conjugate comprising the ligand-binding receptors, the nucleic acid and a carrier macromolecule. Suitable carrier molecules include water-soluble polymers, most preferably natural or synthetic polysaccharides such as, for example, dextrans. Suitable methods for linking oligonucleotides to carrier macromolecules are described in WO 98/22620 and U.S. Pat. No. 6,207,385.

In a further embodiment the linkage between the receptor and the single-stranded nucleic acid molecule may be formed during the course of the detection procedure by formation of a "reagent complex" containing the receptor, single-stranded nucleic acid and any linking molecules required to link the receptor to the nucleic acid.

The components making up the reagent complex may be added either simultaneously or sequentially during the detection procedure. It is well known in the immunoassay field that reagents can be added sequentially with washing between each addition or simultaneously with a final wash step to remove unbound reagents before detection of specific binding. "Simultaneous" addition of reagents encompasses not only addition of reagents at the same time but also the situation where the reagents are added one after the other but with no intermediate washing steps. Sequential addition of reagents with washing between each addition may give greater sensitivity but simultaneous addition of reagents requires fewer manipulations and is therefore more amenable to automation for high-throughput diagnostic applications.

In one specific embodiment of the method of the invention receptors specific for the target ligand are first added to the sample under test. The receptors are conjugated with a first component of a biological binding pair. The sample is incubated to allow receptor/ligand binding and then washed to remove unbound receptors. Nucleic acid molecules conjugated to the second component of the biological binding pair are then added, the sample incubated to allow the nucleic acid to become linked to the receptor via binding of the first and second components of the biological binding pair then washed to remove unbound nucleic acid. Detection of the single stranded nucleic acid is then carried out. An example of a biological binding pair is biotin/avidin or biotin/streptavidin. Most preferably the single stranded nucleic acid molecule will be conjugated with biotin and the receptor with avidin or streptavidin. The wash step between the addition of receptors and nucleic acid may be omitted, or the two reagents may be added at the same time.

In another specific embodiment receptors specific for the target ligand are first added to the sample under test. The sample is then incubated to allow receptor/ligand binding and then washed to remove unbound receptors. Secondary receptors capable of binding to the first receptors are then added to the sample, these secondary receptors being linked to single stranded nucleic acid marker molecules. The sample is then incubated to allow binding of the secondary receptors to the first receptors and washed to remove unbound secondary receptors. Detection of the nucleic acid is then carried out as described below. A specific example of this embodiment is the use of an antibody as the first receptor, i.e. the receptor which specifically binds the ligand, and an anti-isotype antibody as the secondary receptor. The wash step between the addition of receptors and secondary receptors may be omitted, or the two reagents may be added at the same time.

In a variation of this embodiment the nucleic acid molecules may be linked to the secondary receptors using the reaction between a biological binding pair. For example, the secondary receptor may be conjugated with avidin or streptavidin and the nucleic acid molecule with biotin. Linking of the secondary receptors to the nucleic acid molecules via biotin/avidin or biotin/streptavidin binding may then be effected by addition of the secondary receptors and nucleic acid molecules to the test sample as separate reagents, optionally with a washing step between addition of the two reagents. Alternatively, the secondary receptors may be linked to the nucleic acid molecules in a separate step and the linked reagent added to the test sample.

In a further specific embodiment receptors specific for the target ligand are first added to the sample under test. The sample is then incubated to allow receptor/ligand binding and then washed to remove unbound receptors. Secondary receptors capable of binding to the first receptors are then added to the sample, the secondary receptors being conjugated with the first half of a biological binding pair. The sample is then incubated to allow binding of the secondary receptors to the first receptors and washed to remove unbound secondary receptors. The sample is then contacted first with nucleic acid molecules which are conjugated with both the first half of the biological binding pair at a first end of the nucleic acid strand and the second half of the biological binding pair at a second end of the nucleic acid strand and then with nucleic acid molecules conjugated only with the second half of the bio-logical binding pair. Following a final wash step, the nucleic acid is detected as described below.

A specific example of this embodiment utilises secondary receptors conjugated with streptavidin, a first type of nucleic acid molecules conjugated with biotin at one end of the nucleic acid strand and streptavidin at the other end of the nucleic acid strand and a second type of nucleic acid molecules conjugated with biotin only. It is preferred to add the two types of nucleic acid molecules sequentially with an intermediate washing step even if the remainder of the reagent additions are performed simultaneously, i.e. without intermediate washing steps. In this embodiment the use of the two types of nucleic acid molecules provides an additional round of amplification, as illustrated in the accompanying Figures.

Several of the specific embodiments listed above utilise a "biological binding pair" in order to link together components of the reagent complex. Suitable biological binding pairs include biotin/avidin and biotin/streptavidin. Techniques for the conjugation of proteins and nucleic acids with biotin, streptavidin and avidin are well known in the art. In addition, a number of useful conjugates are commercially available.

Components of the reagent complex may also be linked by way of specific binding, an example being the use of secondary receptors which bind directly to ligand-binding receptors. Components may also be linked with the use of bi-specific linker molecules. An example of a bi-specific linker is a recombinant protein A/streptavidin chimeric protein, described in U.S. Pat. No. 5,328,985. This chimeric molecule is capable of binding both an antibody, via the protein A domain, and a biotinylated molecule, via the streptavidin domain.

Once the binding reaction part of the method is complete the presence of specific ligand/receptor complexes is detected by detection of the nucleic acid marker molecules.

In a preferred embodiment detection of the nucleic acid is carried out by amplifying a sequence of the nucleic acid and detecting the amplification products. Most preferably, amplification is performed using an isothermal amplification technique.

The most preferred amplification technique is nucleic acid sequence-based amplification (abbreviated to NASBA) but other isothermal amplification techniques may be used such as, for example, transcription mediated amplification, signal-mediated amplification of RNA technology, split promoter amplification reaction, and isothermal solution phase amplification. The NASBA technique is well known in the art, as described by Compton, J. Nature. 350: 91-92 (1991) and Davey et al., U.S. Pat. No. 5,409,818). NASBA is generally used with a single-stranded RNA marker and the amplification products are single-stranded RNA. However, in the present invention the target is, preferably, single-stranded DNA providing single-stranded RNA amplification products.

NASBA is an effective procedure for generating large quantities of RNA corresponding to a target nucleic acid sequence in vitro, allowing detection of target sequences that are present in very low concentrations in the original test sample. The NASBA method is based on the use of a primer which is modified with a promoter sequence, for example a T7 promoter. The sensitivity and specificity of the NASBA amplification has been shown to be the same as for PCR and better than most RT-PCR protocols.

In a most preferred embodiment, detection of the nucleic acid is performed by amplification of a region of the nucleic acid and real-time detection of the amplification products. Most preferably, detection of the nucleic acid will be carried out by real-time NASBA. The NASBA reaction results in the generation of amplification products, the major amplification product being antisense single-stranded RNA corresponding to a region of the target nucleic acid. Real-time NASBA involves detection of the amplification products concurrently with target amplification. This is possible with the use of "molecular beacons" technology in combination with standard NASBA amplification, as described by Leone et al., Nucleic Acids Research. 26: 2150-2155 (1998).

A combination of an isothermal amplification reaction with real-time detection of the amplification products provides extreme sensitivity. This improved sensitivity enables, for example, the performance of in situ detection of very low levels of target analytes, e.g. proteins or antibodies. Furthermore, it is possible to perform precise directly quantitative detection, even of very low levels of the target analyte.

It will be appreciated that the precise nature of the nucleic acid marker molecule, i.e. its sequence is not material to the invention. If NASBA is to be used for detection of a single-stranded RNA marker it is generally preferable to avoid RNA sequences which would lead to the formation of extensive secondary structure which may interfere with the efficiency of the amplification reaction.

The method of the invention has a major advantage over the previously known immuno-PCR technique in that it is possible to perform substantially isothermal amplification of single-stranded nucleic acids, for example using the NASBA reaction, and it is not necessary to heat to high temperatures of ~95° C. during the amplification reaction. The high temperatures required for the denaturation of double-stranded DNA in the denaturation step of the PCR cycle are a disadvantage when it comes to immuno-PCR detection of immobilised antigens, since the high temperatures may lead to degradation of the antigen and/or the antibody used in the immunological detection. This problem is avoided by detection of a single-stranded nucleic acid target by an isothermal NASBA reaction.

The method of the invention finds utility in the field of immunological detection, especially in the diagnostics field. In particular, the method can be adapted to perform an immunoassay analogous to a standard sandwich ELISA test. A sandwich ELISA generally requires two antibodies that are directed against a particular antigen. One antibody is passively adsorbed (coated) onto the surface of the wells of a microtitre assay plate. The wells are then blocked with a non-specific blocking agent to reduce background non-specific binding of the assay reagents. Test samples suspected of containing the desired antigen (ligand) are then added to the wells and incubated for sufficient time to allow the antigen to bind to the antibody immobilised on the surface of the plate. After washing to remove unbound reagents a second antibody (receptor) is added to the wells. This second antibody binds to the immobilized antigen completing the sandwich. Binding of the second antibody (the receptor) to the antigen (the ligand) is then carried out using the method of the invention, i.e. by formation of a reagent complex linking the second antibody (receptor) to a nucleic acid which is then detected in the detection step of the assay.

In other types of ELISA the test sample may be added directly to the wells of the microtitre plate and incubated to allow antigen (ligand) present in the sample to become bound to the surface of the wells. This type of assay is similar to the sandwich assay but does not require the first antibody, instead the antigen is coated directly onto the surface of the microtitre plate.

The "test sample" to be tested for the presence of a particular ligand may be essentially any material it is desired to test for the presence of a ligand. It may be a fluid sample, such as a clinical sample, an environmental fluid etc. For example, in the diagnostics field the test sample may comprise body fluids such as whole blood, serum, plasma, lymph, tears, urine etc. The test sample may also be a solid sample such as, for example, a tissue section, fixed cells or a cell smear, as discussed below. The precise nature of the test sample is not material to the invention.

The method of the invention can also be adapted for use in immunohistochemistry, for example detection of a ligand in situ in a fixed and sectioned tissue sample, and the word "sample" as used in the claims is to be interpreted accordingly as incorporating tissue samples and sections, fixed cells, cell smears etc. When the method of the invention is used for in situ ligand detection in a tissue sample it is preferred to use NASBA amplification for detection of the nucleic acid marker molecule, most preferably a single-stranded RNA marker. The major goals of in situ analysis are to determine the location of the antigen, to protect and not degrade the target and to maintain the morphology of the tissue. The use of immuno-PCR to detect antigens in situ may result in degradation of the antigen or the antibody used in the assay and damage to the underlying morphology of the tissue because of the need to include a high temperature step in the PCR reaction cycle. Use of NASBA to detect an RNA marker according to the method of the invention avoids these problems since NASBA is an essentially isothermal amplification technique and can be performed at a constant temperature of around 42° C. (Davey et al, U.S. Pat. No. 5,409,818). Thus there is no need for high temperature denaturation steps.

A specific example of the application of the method of the invention to in situ antigen detection is in the detection of different levels of the tumour suppressor protein p53 in ovarian carcinoma as a prognostic marker. By using a highly specific monoclonal antibody against the p53 antigen located in situ in a tumour tissue section in combination with a streptavidin labelled secondary antibody attached to a biotin labelled nucleic acid marker such as a DNA or RNA marker, it may be possible to detect changes in p53 expression level of below 10 proteins. Detection of the nucleic acid marker attached to the secondary antibody (via biotin/streptavidin binding) is preferably carried out by performing NASBA using an ideal primer pair and an ideal molecular beacon probe. The fluorescent signal from the bound molecular beacon probe may be detected using a normal fluorescent microscope fitted with a CCD camera and software.

Embodiments of the present invention will now be described, by way of example only, with reference to the accompanying drawings, in which:

FIG. 1 is a schematic representation of conjugates used in ligand detection reactions according to the invention.

FIG. 2 is a schematic representation of examples of different linkers (avidine-biotin, streptavidin-biotin, dextran or direct conjugation via chemical bonds) that may be used as a bridge between the second receptor and the nucleic acid oligo. The single-stranded oligo is then amplified by NASBA utilising primers and molecular beacons for real time detection as set out more fully in the following examples.

FIG. 3 is a schematic representation of various conjugates including different linkers that may be utilised in ligand detection reactions according to the invention.

FIG. 4 is a general illustration of the ligand detection reaction utilising NASBA amplification and molecular beacon technology according to the invention.

Figure 1:
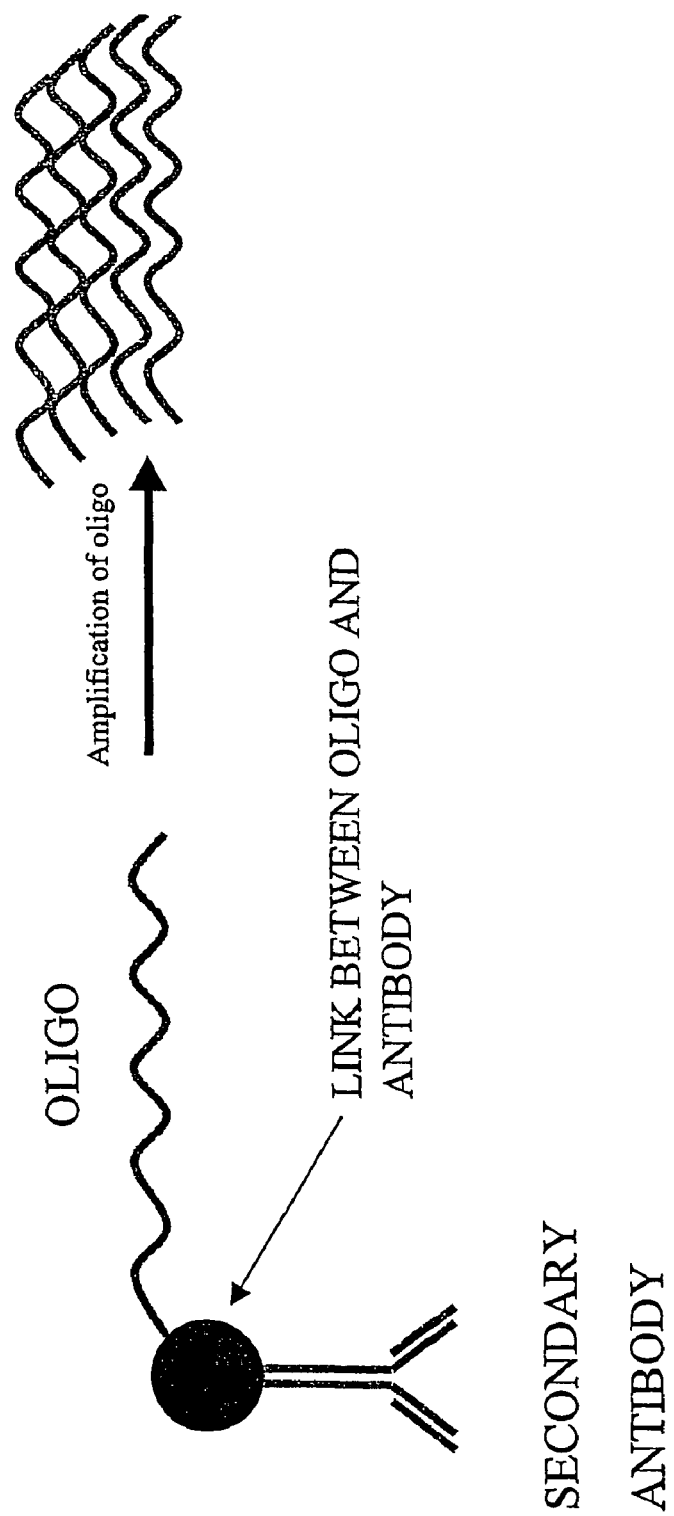

In the general ligand detection reaction described and illustrated in the Figures target ligand (antigen) immobilised on a solid surface is bound by first antibody having specificity for the antigen. A second antibody having specificity for the first antibody (e.g. an anti-isotype antibody) is then bound to the first antibody. The second antibody is conjugated to the single-stranded DNA oligo via one of a number of different linkers as set out in FIGS. 2 and 3. The single-stranded DNA oligo is then amplified by NASBA utilising primers and molecular beacons for real time detection as shown in FIG. 4 and set out more fully in the following examples.

The invention will be further understood with reference to the following experimental examples:

EXAMPLE 1

Immuno Real-Time NASBA Amplification

Materials and Reagents
Microplates: Greiner nr. 650161, 96-well, U-bottom
Microtubes: MCT-150-C 1.5 ml clear (Axygen Scientific nr. 311-08-051)
Phosphate Buffered Saline tablets (PBS): 0.01M pH 7.4 (Sigma P-4417)
Phosphate Buffered Saline with Tween 20 (PBST):
0.01M pH 7.4 (Sigma P-3563)
Blocking Buffer: 0.25 mg/ml Bovine Serum Albumin (BSA) in PBS (Sigma B-6917)
Antibody Dilution Buffer: 0.01M PBS
Primary Antibody (1): Goat-anti-Salmonella
(Europa Bioproducts Ltd., CR7100GAP)
10 µg/ml in PBS
Culture of bacteria (antigen):
Salmonella cholerasuis subs. cholerasuis
Diluted 1:100; 1:100 and 1:10.000 in PBS
DSM nr. 4883 (DSMZ: Deutsche Sammlung von Mikroorganismen und Zellkulturen GmbH)
Primary Antibody (2): Rabbit-anti-Salmonella
(Europa Bioproducts Ltd., CR7100RP)
1 µg/ml in PBS
Secondary Antibody (ELISA): Goat-anti-Rabbit Alkaline Phosphatase (AP) Conjugate
(Zymed Laboratories Inc., 81-6122)
1:2000 in PBS
PNPP (100×)-Substrate for Alk. Phosphatase:
(Zymed Laboratories Inc., 00-2201)
Diluted 1:100 in Substrate Buffer (10×) for PNPP
Substrate Buffer (10×) for PNPP:
(Zymed Laboratories Inc., 00-2208)
Diluted 1:10 with distilled water.
IMRAMP Conjugate:
Dextran backbone with Goat-anti-Rabbit IgG and synthetic oligonucleotide (see below for the sequence-specification). Two different oligonucleotides have been used in the protocol (Immb5 and Imkort).
IMRAMP Conjugate Dilution Buffer: Tris/HCl 0.1M pH 7.2
Automated Isolation Reagents:
Nuclisens Nasba Diagnostics nr.84044 (Organon Teknika)
Silica particles
Lysis buffer (pH normal)
Synthetic oligo, (MWG Biotech AG) Sequences:

(Immb5): 5' Amino-Modifier C12

5'C12-gattaatcggccggcttcgcctaggcagacatttcagcatac
gcatactatatcctttgcatgctactatatggcagcgtcgtcagatag
cacagtagcagcgattaa-3' (SEQ ID NO: 1)

(Imkort): 5' Amino-Modifier C12

5'C12-gattaatcgggcagacatttcagcatacgcatactatcctttt
gcatgctactatatgtcagatagcacagtagcagcgattaa-3'
(SEQ ID NO: 2)

Molecular Beacons (MWG Biotech AG) Sequence:

(Pmb2): 5' FAM-GCGGC ATC CTT TGC ATG CTA CTA TA
GCCGC-Dabsyl-3' (SEQ ID NO: 3)

NASBA primer 1 and 2 (MWG Biotech AG) Sequences:

(Pnasba1): 5'-AAT TCT AAT ACG ACT CAC TAT AGG GAG
AAG G GCT GCT ACT GTG CTA TCT GA-3' (SEQ ID NO: 4)

(Pnasba2): 5'-GAT GCA AGG TCG CAT ATG AG GAC ATT
TCA GCA TAC GCA TA-3' (SEQ ID NO: 5)

Basic kit (Amplification reactions):
Nuclisens Nasba Diagnostics nr. 84121 (Organon Teknika)
Protocols
Coating Plates
1. Coat the wells of a 96-well microtiter plate with 100 µl of 10 µg/ml primary antibody (1). Incubate overnight at 41° C.
2. Discard the uncoated primary antibody (1); wash the coated wells at least three times with PBST and one time with PBS.
3. Block remaining active sites by incubating the plate with 200 µl 0.25 mg/ml BSA for two hours at 20° C.
4. Discard the unblocked BSA; wash the coated wells at least three times with PBST and one time with PBS.
The microplate is now ready to be used in ELISA or IMRAMP applications, as described below.
Sandwich ELISA (Enzyme Linked Immuno Sorbent Assay) (Function as a Control at Step 1-8 in IMRAMP)
5. Add 70 µl of the appropriate concentration of a fresh Salmonella-culture to the wells. Incubate 1 hour 20° C. with shaking (40 rev/min)
6. Discard the unbound bacteria; wash the coated wells at least three times with PBST and once with PBS.
7. Prepare appropriate dilution of primary antibody (2) in PBS. Add 70 µl to the wells and incubate for 1 hour 20° C. with shaking (40 rev/min)
8. Discard the unbound primary antibody (2); wash the coated wells at least three times with PBST and once with PBS.
9. Prepare the appropriate dilution of secondary antibody Alkaline Phophatase (AP) conjugate. Add 70 µl to the wells and incubate for 1 hour 20° C. with shaking (40 rev/min)
10. Discard the unbound secondary antibody; wash the coated wells at least three times with PBST and once with PBS.
11. Prepare the p-nitrophenyl phosphate (PNPP)-substrate for Alkaline Phophatase (AP) in PNPP-substrate buffer (10×)
12. Yellow colour development occurs in positive samples. Negative samples appear clear/do not show colour development.
Immuno Real-Time Amplification (IMRAMP)
5. Add 70 µl of the appropriate concentration of a fresh Salmonella-culture to the wells. Incubate 1 hour at 20° C. with shaking
6. Discard the unbound bacteria; wash the coated wells at least three times with PBST and once with PBS.
7. Prepare the appropriate dilution of primary antibody (2) in PBS. Add 70 µl to the wells and incubate for 1 hour 20° C. with shaking (40 rev/min).
8. Discard the unbound primary antibody (2); wash the coated wells at least three times with PBST and once with PBS.

9. Prepare appropriate dilution of IMRAMP Conjugate in Tris/HCl, (description of conjugate given above). Add 70 µl to the wells and incubate for 1 hour 20° C. with shaking (40 rev/min).
10. Discard the unbound IMRAMP Conjugate; wash the coated wells at least three times with PBST and once with PBS.

The microplate is now ready to be used in application (A) or (B) as described below:

(A) IMRAMP with NASBA-Amplification and Molecular Beacons Detection (FIG. 4)
1. Prepare the mastermix: Follow the instructions from Nuclisens Amplification kit.
Add the following solutions to the mastermix:
2.5 µl of a 20 µM Molecular Beacons (Pmb2) towards the syntetic oligo
5 µl of a 10 µM Nasba primer 1 towards the synthetic oligo
5 µl of a 10 µM Nasba primer 2 towards the synthetic oligo
60 µl enzyme-solution (RNA-polymerase; Rnase H; Reverse Transcriptase)
2. Add 20 µl PBS to the wells.
3. Add 15 µl mastermix to the wells (see above)
4. Add Rnasin to the well at a final concentration: 1 U/microliter
5. Amplification and detection proceed at 41° C. in a BIO-TEK FL600 Fluorescence Plate Reader for 2 hours.
Configuration of the Plate Reader:
Sensitivity: 75
Excitation: 485/40
Emission: 530/25

(B) IMRAMP with Extraction: NASBA-Amplification and Molecular Beacons Detection
1. Add 100 µl lysis buffer to the wells and incubate for 20 min at 37° C.
2. Transfer all the material from the wells to separate tubes containing 0.9 ml lysis buffer. Incubate 10 min at 37° C.
3. Add 50 µl silica particles to each tube and incubate for 10 min at room temperature. Mix the tubes every 2 minutes.
4. Discard all the material from the tube in a separate cartridge for use in the Nuclisens Extractor.
5. Follow the manual for the method: "Extraction of 1 ml plasma".
6. 5 µl extract will be used in the NASBA amplification method (described in A).

Note:
Lysis buffer is added to the wells after incubation with IMRAMP Conjugate and before the usual exctraction method (Nuclisens).

Lysis buffer probably destroys the dextran backbone, and therefore reduces possible steric obstacles for RNA polymerase.

EXAMPLE 2

Amiplification of Oligos in Conjugates Containing a Dextran Backbone with ssDNA and Antibody Using Different Sizes of Dextran The following conjugates were prepared:

| Conjugate | Oligo | Dextran size (mol weight) |
|---|---|---|
| 641101 | Immkort | 20 000 |
| 641101 | Immkort | 196 000 |
| 641101 | Immkort | 500 000 |
| 641101 | Pnsabal | 500 000 |

Amplification
Mastermix: 2× reagent spheres
160 µl diluent
27 nasba water
28 KCl
120 enzyme divided in 2 and added:
1) 2.5 Pnasba2, (NASBA primer 2) 10 µM
2.5 Immkort 0.1 µM (used as NASBA primer 1)
1.25 Pmb2ny, (molecular beacon) 20 µM
2) 15 µl P nasba 1+P nasba 2 primermix, 10 µM
15 µl of the mastermix was loaded into each well. Samples and conjugates were added and products were detected in a BIO-TEK FL 6000 fluorescence plate reader.

Results (not shown) indicate that the smaller molecular weight dextrans are best suited for NASBA detection

EXAMPLE 3

Extraction and Amplification of Conjugates

Extraction of Samples:
100 µl conjugate was added to 900 µl lysis buffer (NucliSens, pH normal)
Incubated in a waterbath for 10 minutes at 37° C.
Conjugate in lysis buffer was added to 50 µl of silica and incubated for 10 minutes inverting the tubes every 2 minutes.
The samples were loaded onto the Nuclisens Extractor and RNA/DNA was extracted using standard methods.
Results from the NASBA Amplification:

| Conjugate | Containing | Additives | Result NASBA |
|---|---|---|---|
| F470301-2 | Immb3, dx, Ab | Tris HCl, NaCl, bronidox | Negative |
| F650301-2 | Imm5, dx | Tris HCl, NaCl | Negative |
| F320401 (B) | Imm5, dx, Ab | Tris HCl, NaCl | Negative |
| F230701-1 | Imkort, dx, Ab | EDTA, RNasin, DMSO | Amplified |
| F230701-2 | Imkort, dx, Ab | EDTA, RNasin, DMSO | Amplified |
| F230701-1* | Imkort, dx, Ab | EDTA, RNasin | Amplified |
| F230701-1** | Imkort, dx, Ab | RNasin, DMSO | Amplified |
| F230701-1*** | Imkort, dx, Ab | EDTA, DMSO | Negative |

Immb3 oligo
dx dextran
Ab Antibody
Bronidox preservative

Amplification results (not shown) indicate that sucessful amplification can be achieved using extracted dextran conjugates. Conjugates containing EDTA, RNasin and DMSO are best suited for NASBA amplification in IMRAMP.

EXAMPLE 4

Amplification with/without Rnasin

Amplification of oligo, Psek2 and conjugate F320401. F320401 consists of Immb3 (oligo), dextran and GAR (antibody).
Mastermix:
1 reagent sphere
80 µl reagent sphere diluent 13.5 µl nasbawater 14 µl KCl 5 µl Pnasba primer 1

5 µl Pnasba primer 2

2.5 µl Pmb2 (molecular beacon)

60 µl enzyme

Split the mastermix in two halves. One half was added RNasin with final concentration 1 U/µl.

15 µl of the mastermix was loaded into each well and added 5 µl.

Samples:

| | | |
|---|---|---|
| 1) | Psek2 (1:100) | |
| 2) | Psek2 (1:10.000) | mastermix without RNasin |
| 3) | F320401 | |
| 4) | Psek2 (1:100) | |
| 5) | Psek2 (1:10.000) | mastermix with RNasin |
| 6) | F320401 | |

Results (not shown) indicate that Rnasin promotes amplification.

EXAMPLE 5

Amplification with/without Heating

Amplification of artificial oligo, Psek2 and conjugates, F620301 and F650301-2.

F620301 consists of Immb5 (oligo) on dextran.

F650301-2 consists of Immb5 dextran and GAR (antibody).

The conjugates are dissolved in Tris/HCl and NaCl.

Mastermix:

2 reagent spheres

160 µl reagent sphere diluent

27 µl nasbawater

28 µl KCl

10 µl nasbaprimer 1: Pnasba1

10 µl nasbaprimer 2: Pnasba 2

5 µl molecular beacons: Pmb2

10 µl of the mastermix was loaded into each of 20 wells and added 5 µl sample: oligo or conjugate in two groups. In group 1 the enzyme was added directly (without preheating). In group 2, the mastermix was preheated to 65° C. for 4 minutes and cooled to 41° prior to adding the enzyme. Both groups of samples were amplified and detected at 41° C. for 2 hours.

Results (not shown) confirm that NASBA amplification of the artificial oligo is best performed without preheating of the mastermix.

The invention claimed is:

1. A method for detecting a ligand in a sample, which method comprises steps of:
   (a) contacting the sample with reagents capable of forming a reagent complex, which reagent complex comprises a receptor capable of specifically binding to said ligand, said receptor is linked to a nucleic acid molecule; and
   (b) detecting any complexes formed by binding of the receptor part of said reagent complex to ligand present in the sample by specifically detecting the presence of the nucleic acid molecule by amplifying a region of the nucleic acid using a nucleic acid sequence based amplification reaction (NASBA) and simultaneously detecting products of the amplification reaction in real-time.

2. A method according to claim 1 wherein step (a) comprises sequential or simultaneous steps of:
   (i) contacting the sample with receptors capable of binding to said ligand, said receptors being conjugated with a first component of a biological binding pair; and
   (ii) contacting the sample with nucleic acid molecules conjugated with a second component of a biological binding pair.

3. A method according to claim 1 wherein step (a) comprises sequential or simultaneous steps of:
   (i) contacting the sample with receptors capable of binding to said ligand; and
   (ii) contacting the sample with secondary receptors capable of binding to the receptors of part (i), said secondary receptors being linked to nucleic acid molecules.

4. A method according to claim 1 wherein step (a) comprises sequential or simultaneous steps of:
   (i) contacting the sample with receptors capable of binding to said ligand;
   (ii) contacting the sample with secondary receptors capable of binding to the receptors of part (i), said secondary receptors being conjugated with a first member of a biological binding pair; and
   (iii) contacting the sample with single stranded nucleic acid molecules conjugated with a second member of a biological binding pair.

5. A method according to claim 1 wherein step (a) comprises sequential or simultaneous steps of:
   (i) contacting the sample with receptors capable of binding to said ligand;
   (ii) contacting the sample with secondary receptors capable of binding to the receptors of part (i), said secondary receptors being conjugated with a first member of a biological binding pair;
   (iii) contacting the sample with nucleic acid molecules conjugated with a first member of a biological binding pair at one end and a second member of a biological binding pair at the other end of the nucleic acid strand; and
   (iv) contacting the sample with nucleic acid molecules conjugated with a second member of the biological binding pair only.

6. A method according to claim 2, wherein the first and second components of the biological binding pair are streptavidin or avidin and biotin, or vice versa.

7. A method according to claim 3 wherein said secondary receptor is linked to said nucleic acid molecules by a direct chemical bond.

8. A method according to claim 1 wherein step (a) comprises the addition of a reagent complex which is a conjugate comprising receptors capable of binding to the ligand, nucleic acid molecules and a carrier macromolecule.

9. A method according to claim 8 wherein the carrier macromolecule is a dextran.

10. A method according to claim 1 wherein the receptors capable of binding to said ligand are antibodies or antibody fragments.

11. A method according to claim 1 wherein the nucleic acid is partially or completely single-stranded.

12. A method according to claim 11 wherein the nucleic acid is a single-stranded DNA or RNA.

13. A method according to claim 3, wherein the first and second components of the biological binding pair are streptavidin or avidin and biotin, or vice versa.

14. A method according to claim 4, wherein the first and second components of the biological binding pair are streptavidin or avidin and biotin, or vice versa.

15. A method according to claim 5, wherein the first and second components of the biological binding pair are streptavidin or avidin and biotin, or vice versa.

* * * * *

SEQUENCE LISTING

<160> NUMBER OF SEQ ID NOS: 5

<210> SEQ ID NO 1
<211> LENGTH: 108
<212> TYPE: DNA
<213> ORGANISM: Artificial
<220> FEATURE:
<223> OTHER INFORMATION: synthetic oligonucleotide

<400> SEQUENCE: 1
gattaatcgg ccggcttcgc ctaggcagac atttcagcat acgcatacta tatcctttgc     60
atgctactat atggcagcgt cgtcagatag cacagtagca gcgattaa                 108

<210> SEQ ID NO 2
<211> LENGTH: 83
<212> TYPE: DNA
<213> ORGANISM: Artificial
<220> FEATURE:
<223> OTHER INFORMATION: synthetic oligonucleotide

<400> SEQUENCE: 2
gattaatcgg gcagacattt cagcatacgc atactatcct ttgcatgcta ctatatgtca     60
gatagcacag tagcagcgat taa                                             83

<210> SEQ ID NO 3
<211> LENGTH: 30
<212> TYPE: DNA
<213> ORGANISM: Artificial
<220> FEATURE:
<223> OTHER INFORMATION: synthetic oligonucleotide

<400> SEQUENCE: 3
gcggcatcct ttgcatgcta ctatagccgc                                      30

<210> SEQ ID NO 4
<211> LENGTH: 51

-continued

```
<212> TYPE: DNA
<213> ORGANISM: Artificial
<220> FEATURE:
<223> OTHER INFORMATION: synthetic oligonucleotide

<400> SEQUENCE: 4
aattctaata cgactcacta tagggagaag ggctgctact gtgctatctg a            51

<210> SEQ ID NO 5
<211> LENGTH: 40
<212> TYPE: DNA
<213> ORGANISM: Artificial
<220> FEATURE:
<223> OTHER INFORMATION: synthetic oligonucleotide

<400> SEQUENCE: 5
gatgcaaggt cgcatatgag gacatttcag catacgcata                          40
```